US010408836B2

(12) United States Patent
Weiss et al.

(10) Patent No.: US 10,408,836 B2
(45) Date of Patent: Sep. 10, 2019

(54) METHODS OF DETECTING INFLUENZA VIRUS

(71) Applicant: University of Cincinnati, Cincinnati, OH (US)

(72) Inventors: Alison A. Weiss, Cincinnati, OH (US); Karen Melissa Gallegos Villalobos, Cincinnati, OH (US); David Ralph, Cincinnati, OH (US)

(73) Assignees: University of Cincinnati, Cincinnati, OH (US); MicrobeCapture, LLC, Cincinnati, OH (US)

( * ) Notice: Subject to any disclaimer, the term of this patent is extended or adjusted under 35 U.S.C. 154(b) by 0 days.

(21) Appl. No.: 15/285,565

(22) Filed: Oct. 5, 2016

(65) Prior Publication Data

US 2017/0016899 A1 Jan. 19, 2017

Related U.S. Application Data

(62) Division of application No. 14/211,549, filed on Mar. 14, 2014, now Pat. No. 9,487,816.

(60) Provisional application No. 61/790,306, filed on Mar. 15, 2013.

(51) Int. Cl.

| | |
|---|---|
| ***A61K 39/12*** | (2006.01) |
| ***G01N 33/569*** | (2006.01) |
| ***C12Q 1/34*** | (2006.01) |
| ***G01N 33/50*** | (2006.01) |
| ***C12N 9/24*** | (2006.01) |
| ***C12Q 1/02*** | (2006.01) |

(52) U.S. Cl.

CPC ..... *G01N 33/56983* (2013.01); *C12N 9/2402* (2013.01); *C12Q 1/025* (2013.01); *C12Q 1/34* (2013.01); *G01N 33/5017* (2013.01); *C12N 9/24* (2013.01); *C12Y 302/01018* (2013.01); *G01N 2333/11* (2013.01); *G01N 2333/924* (2013.01)

(58) Field of Classification Search

USPC ........................................................ 424/186.1

See application file for complete search history.

(56) References Cited

U.S. PATENT DOCUMENTS

| | | | |
|---|---|---|---|
| 4,029,763 | A | 6/1977 | Kilbourne |
| 7,081,352 | B2 | 7/2006 | Shimsaki et al. |
| 2011/0189655 | A1 | 8/2011 | Li et al. |

FOREIGN PATENT DOCUMENTS

| | | |
|---|---|---|
| WO | 2011143262 | 11/2011 |

OTHER PUBLICATIONS

Nayak and Reichl Neuraminidase activity assays for monitoring MDCK cell culture derived influenza virus. J. Virolog. Met. 2014; 122:9-15.*

(Continued)

*Primary Examiner* — Janet L Andres
*Assistant Examiner* — Stuart W Snyder
(74) *Attorney, Agent, or Firm* — Dinsmore & Shohl LLP

(57) ABSTRACT

Provided herein is a method of detecting the presence of influenza virus in a sample while minimizing false positives due to presence of one or more other pathogens in the sample, the method including measuring the enzymatic activity of neuraminidase (NA) in the sample under one or more differentiating conditions selected from the group consisting of pH, binding to anti-NanA antibody, size exclusion, hemagglutinin (HA) binding, chemical inhibition, and combinations thereof.

4 Claims, 11 Drawing Sheets

Specification includes a Sequence Listing.

(56) References Cited

OTHER PUBLICATIONS

Wickramasinghe et al. Tangential Flow Microfiltration and Ultrafiltration for Human Influenza A Virus Concentration and Purification. Biotech. Bioeng. 2005; 92(2): 199-208.*

Stiver, The treatment of influenza with antiviral drugs. CMAJ • Jan. 7, 2003; 168 (1): 49-57.*

Nagai et al, "Comparison of Substrate Specificities of Sialidase Activity between Purified Enzymes from Influenza Virus A (H1N1 and H3N2 subtypes) and B Strains and Their Original Viruses, " Biol. Pharm. Bull. 1995; 18(9): 1251-1254.

Takahashi et al, "Duck and Human Pandemic Influenza A Viruses Retain Sialidase Activity under Low pH Conditions," 2001; J. Biochem. 130: 279-283.

Fukui et al, "Neuraminidase Activity in Some Bacteria from the Human Mouth," Archs Oral Biol. 16: 1361-1365, Pergamon Press, Great Britain (1971).

Hoglund et al, "Effect of Parainfluenza-3 virus Neuraminidase on the Structure of the Gel Phase of Bovine Nasal Secretion," Infect. Immun. 10(4): 877-882 (1974).

Fiore et al, "Antiviral Agents for the Treatment and Chemoprophylaxis of Influenza Recommendations of the Advisory Committee on Immunization Practices (ACIP), MMWR Recommendations and Reports," vol. 60 (1): 1-24 (2011), Centers for Disease Control and Prevention.

Yen et al, "Importance of Neuraminidase Active-Site Residues to the Neuraminidase Inhibitor Resistance Influenza Viruses," J. Virol. 80: 8787-8795 (2006).

Solman, "New antivirals and Drug Resistance," Annu. Rev. Biochem. 78: 95-118 (2009).

Pizzomo et al, "Influenza Drug Resistance," Sem. Res. Crit Care Med. 409-422 (2011).

* cited by examiner

A

B

SEQUENCE LISTING

```
<160> NUMBER OF SEQ ID NOS: 4

<210> SEQ ID NO 1
<211> LENGTH: 24
<212> TYPE: DNA
<213> ORGANISM: Streptococcus pneumoniae

<400> SEQUENCE: 1

catatggctt taacagagaa aacg                                   24
```

<210> SEQ ID NO 2
<211> LENGTH: 26
<212> TYPE: DNA
<213> ORGANISM: Streptococcus pneumoniae

<400> SEQUENCE: 2
aagcttattt ttgctcaaaa attccc 26

<210> SEQ ID NO 3
<211> LENGTH: 1375
<212> TYPE: DNA
<213> ORGANISM: Streptococcus pneumoniae

<400> SEQUENCE: 3
gacatattcg aaagcgggcg taacggtaac ccaaataaag atggaatcaa gagttatcgt 60
attccagcac ttctcaagac agataaagga actttgatcg caggtgcaga tgaacgccgt 120
ctccattcga gtgactgggg tgatatcggt atggtcatca gacgtagtga agataatggt 180
aaaacttggg gtgaccgagt aaccattacc aacttacgtg acaatccaaa agcttctgac 240
ccatcgatcg gttcaccagt gaatatcgat atggtgttgg ttcaagatcc tgaaaccaaa 300
cgaatctttt ctatctatga catgttccca gaagggaagg gaatctttgg aatgtcttca 360
caaaaagaag aagcctacaa aaaaatcgat ggaaaaacct atcaaatcct ctaccgtgaa 420
ggagaaaagg gagcttatac cattcgagaa aatggtactg tctatacacc agatggtaag 480
gcgacagact atcgcgttgt tgtagatcct gttaaaccag cctatagcga caagggtgat 540
ctatacaagg gtgaccaatt actaggaaat atctacttca caacaaacaa aacttctcca 600
tttagaattg ccaaggatag ctatctatgg atgtcctaca gtgatgacga cgggaagaca 660
tggtcagctc ctcaagatat tactccgatg gtcaaagccg attggatgaa attcttgggt 720
gtaggtcctg gaacaggaat tgtacttcgg aatgggcctc acaagggacg gattttgata 780
ccggtttata cgactaataa tgtatctcac ttagatggct cgcaatcttc tcgtgtcatc 840
tattcagatg atcatggaaa aacttggcat gctggagaag cggtcaacga taaccgtcag 900
gtagacggtc aaaagatcca ctcttctacg atgaacaata gacgtgcgca aaatacagaa 960
tcaacggtgg tacaactaaa caatggagat gttaaactct ttatgcgtgg tttgactgga 1020
gatcttcagg ttgctacaag taaagacgga ggagtgactt gggagaagga tatcaaacgt 1080
tatccacagg ttaaagatgt ctatgttcaa atgtctgcta tccatacgat gcacgaagga 1140
aaagaataca tcatcctcag taatgcaggt ggaccgaaac gtgaaaatgg gatggtccac 1200
ttggcacgtg tcgaagaaaa tggtgagttg acttggctca aacacaatcc aattcaaaaa 1260
ggagagtttg cctataattc gctccaagaa ttaggaaatg gggagtatgg catcttgtat 1320
gaacatactg aaaaaggaca aaatgcctat accctatcat ttagaaaatt taatt 1375

<210> SEQ ID NO 4
<211> LENGTH: 470
<212> TYPE: PRT
<213> ORGANISM: Streptococcus pneumoniae

<400> SEQUENCE: 4

Phe Lys Arg Ser Asp Leu Glu Lys Lys Leu Pro Glu Gly Ala Ala Leu
1 5 10 15

Thr Glu Lys Thr Asp Ile Phe Glu Ser Gly Arg Asn Gly Lys Pro Asn
20 25 30

-continued

```
Lys Asp Gly Ile Lys Ser Tyr Arg Ile Pro Ala Leu Leu Lys Thr Asp
        35                  40                  45

Lys Gly Thr Leu Ile Ala Gly Ala Asp Glu Arg Arg Leu His Ser Ser
    50                  55                  60

Asp Trp Gly Asp Ile Gly Met Val Ile Arg Arg Ser Glu Asp Asn Gly
65                  70                  75                  80

Lys Thr Trp Gly Asp Arg Val Thr Ile Thr Asn Leu Arg Asp Asn Pro
                85                  90                  95

Lys Ala Ser Asp Pro Ser Ile Gly Ser Pro Val Asn Ile Asp Met Val
            100                 105                 110

Leu Val Gln Asp Pro Glu Thr Lys Arg Ile Phe Ser Ile Tyr Asp Met
        115                 120                 125

Phe Pro Glu Gly Lys Gly Ile Phe Gly Met Ser Ser Gln Lys Glu Glu
    130                 135                 140

Ala Tyr Lys Lys Ile Asp Gly Lys Thr Tyr Gln Ile Leu Tyr Arg Glu
145                 150                 155                 160

Gly Glu Lys Gly Ala Tyr Thr Ile Arg Glu Asn Gly Thr Val Tyr Thr
                165                 170                 175

Pro Asp Gly Lys Ala Thr Asp Tyr Arg Val Val Val Asp Pro Val Lys
            180                 185                 190

Pro Ala Tyr Ser Asp Lys Gly Asp Leu Tyr Lys Gly Asn Gln Leu Leu
        195                 200                 205

Gly Asn Ile Tyr Phe Thr Thr Asn Lys Thr Ser Pro Phe Arg Ile Ala
    210                 215                 220

Lys Asp Ser Tyr Leu Trp Met Ser Tyr Ser Asp Asp Asp Gly Lys Thr
225                 230                 235                 240

Trp Ser Ala Pro Gln Asp Ile Thr Pro Met Val Lys Ala Asp Trp Met
                245                 250                 255

Lys Phe Leu Gly Val Gly Pro Gly Thr Gly Ile Val Leu Arg Asn Gly
            260                 265                 270

Pro His Lys Gly Arg Ile Leu Ile Pro Val Tyr Thr Thr Asn Asn Val
        275                 280                 285

Ser His Leu Asn Gly Ser Gln Ser Ser Arg Ile Ile Tyr Ser Asp Asp
    290                 295                 300

His Gly Lys Thr Trp His Ala Gly Glu Ala Val Asn Asp Asn Arg Gln
305                 310                 315                 320

Val Asp Gly Gln Lys Ile His Ser Ser Thr Met Asn Asn Arg Arg Ala
                325                 330                 335

Gln Asn Thr Glu Ser Thr Val Val Gln Leu Asn Asn Gly Asp Val Lys
            340                 345                 350

Leu Phe Met Arg Gly Leu Thr Gly Asp Leu Gln Val Ala Thr Ser Lys
        355                 360                 365

Asp Gly Gly Val Thr Trp Glu Lys Asp Ile Lys Arg Tyr Pro Gln Val
    370                 375                 380

Lys Asp Val Tyr Val Gln Met Ser Ala Ile His Thr Met His Glu Gly
385                 390                 395                 400

Lys Glu Tyr Ile Ile Leu Ser Asn Ala Gly Gly Pro Lys Arg Glu Asn
                405                 410                 415

Gly Met Val His Leu Ala Arg Val Glu Glu Asn Gly Glu Leu Thr Trp
            420                 425                 430

Leu Lys His Asn Pro Ile Gln Lys Gly Glu Phe Ala Tyr Asn Ser Leu
        435                 440                 445
```

-continued

```
Gln Glu Leu Gly Asn Gly Glu Tyr Gly Ile Leu Tyr Glu His Thr Glu
    450                 455                 460

Lys Gly Gln Asn Ala Tyr
465                 470
```

METHODS OF DETECTING INFLUENZA VIRUS

RELATED APPLICATION

This application is a divisional of pending U.S. application Ser. No. 14/211,549, filed Mar. 14, 2014, and claims the benefit under 35 U.S.C. § 119 of U.S. Provisional Application No. 61/790,306 filed Mar. 15, 2013, which application is hereby incorporated by reference in its entirety.

STATEMENT REGARDING FEDERALLY SPONSORED RESEARCH OR DEVELOPMENT

This invention was made with government support under R01 AI089450 awarded by the National Institutes of Health. The government has certain rights in the invention.

FIELD OF THE INVENTION

The presently disclosed subject matter relates to the field of detection of influenza virus. Specifically, the present subject matter relates to methods of detecting influenza virus in a sample under differentiating conditions that minimize false positives due to the presence of one or more other pathogens in the sample.

BACKGROUND OF THE INVENTION

Influenza accounts for approximately 200,000 hospitalizations and 36,000 deaths in the United States each year. The elderly, children under age five, individuals with underlying health problems, and pregnant women are typically at increased risk for severe disease.

Three types of influenza (A, B, and C) are associated with human disease. Influenza C is not considered clinically important, while influenza B is generally self-limiting. In contrast, influenza A can cause severe, often life-threatening disease, and is of significant medical importance. Type A influenza is further divided into subtypes based on two viral surface proteins, hemagglutinin (HA) and neuraminidase (NA), with 16 known HA and 10 NA subtypes. HA and NA influence viral host range and not all HA or NA subtypes are capable of promoting human infection. Human infection is usually limited to viruses with the NA subtypes N1 or N2. Seasonal influenza in humans is predominantly due to HA subtypes H1, H2, and H3, while human disease acquired from avian sources can include H5, H7, and H9. Highly pathogenic avian influenza types H5N1 and H7N9 are of recent concern.

Influenza is highly adept at escaping detection by the immune system. Antigenic variation occurs by two distinct mechanisms. Antigenic drift results as mutations accumulate in the genes for HA and NA, leading to variants that are no longer recognized by antibodies raised against the original form. In contrast, antigenic shift occurs when two different influenza viruses infect the same cell and shuffle their HA or NA genes, creating new combinations. For example, a cell infected with an avian H5N1 virus and an H3N2 virus could generate new H5N2 or H3N1 recombinants. The entire human population is usually extremely susceptible to new recombinants, and antigenic shift can therefore trigger a global pandemic. Three pandemics occurred in the twentieth century: 1918 (H1N1), 1957 (H2N2), and 1968 (H3N2). The 1918 pandemic was devastating and is estimated to have caused the death of over 21 million people. The pandemic strain of 2009, A(H1N1)pdm09, originally called the "swine flu," set off the first global pandemic of the twenty-first century. The extensive antigenic variation of influenza means the influenza vaccine must be reformulated each year using the strains currently in circulation and presents challenges to developing antibody-based diagnostic assays.

Rapid diagnostic tests could greatly reduce the disease burden due to influenza. Since viral shedding occurs before symptoms appear, rapid diagnostic tests for influenza could identify infected individuals before they spread the disease. Isolation of infected individuals has been shown to be especially valuable in settings with a high concentration of highly vulnerable individuals, such as pediatric hospitals and nursing homes. In addition, rapid diagnostics for influenza would improve treatment. In the absence of a diagnosis, patients may be given antibiotics which are only effective against bacterial infections. In addition, antiviral drugs for influenza are only effective if given within 48 hours of onset of symptoms and resistance to antivirals can develop rapidly. The neuraminidase inhibitors oseltamivir (Tamiflu®) and zanamivir (Relenza®) prevent the action of NA, which promotes viral release from infected cells. Recently, resistance to the neuraminidase inhibitors has developed. During the 2008-2009 influenza season the seasonal H1N1 strain was resistant to oseltamivir, while the seasonal H3N2 variant and the novel, pandemic variant of H1N1 were susceptible to oseltamivir. This situation confounds the ability to generate empirical treatment recommendations.

There are two current approaches for influenza diagnosis. The first approach, molecular polymerase chain reaction (PCR)-based methods, detects viral nucleic acids and can provide rapid (2-4 hours) and sensitive identification of viruses. However, PCR tests are expensive and require well-trained personnel, perishable reagents, and sophisticated equipment, making them unsuitable as rapid point-of-care diagnostics. Further, constant change in the viral genome results in the need for constant development and validation of nucleic acid primers. PCR can be used to identify strains with resistance to antiviral drugs, but only after the resistant isolates have been identified and sequenced and primers recognizing the mutations conferring resistance have been developed and validated.

The second approach for influenza diagnosis includes rapid antigen detection assays developed to diagnose seasonal influenza from biological samples. These point-of-care tests can return results in 15 minutes, but have certain limitations. Some commercially available tests detect only influenza A, some detect both influenza A and B but do not distinguish between them, and others detect and distinguish between influenza A and B. At present, commercially available rapid diagnostic tests do not differentiate between seasonal influenza A and highly pathogenic avian influenza. Rapid diagnostic tests are generally highly specific (>90%), but not very sensitive (20%-70%). As a result, the Centers for Disease Control and Prevention (CDC) has advised that negative test results should not be used to make treatment or infection-control decisions, particularly when influenza virus is circulating in a community. Antibody-based rapid tests may fail to detect new isolates resulting from antigenic shift. Further, antibody-based tests may need to be reengineered for new H and N viruses.

A need exists for the development of rapid diagnostic tests that detect influenza in a patient clinical sample regardless of HA or NA subtype, distinguish influenza from other pathogens in order to minimize false positives, and determine susceptibility of influenza subtypes to NA inhibitors such as oseltamivir and zanamivir. Such improved tests would identify infection with sensitive or resistant strains, direct treatment of individuals infected with susceptible isolates, avoid over-use of neuraminidase inhibitors in treating resistant strains of influenza, and minimize inappropriate use of antibiotics, which are ineffective for viral infections.

SUMMARY OF THE INVENTION

Accordingly, provided herein is a method of detecting presence of influenza virus in a sample while minimizing false positives due to presence of one or more other pathogens in the sample, the method comprising measuring the enzymatic activity of neuraminidase (NA) in the sample under one or more differentiating conditions selected from the group consisting of pH, binding to anti-NanA antibody, size exclusion, hemagglutinin (HA) binding, chemical inhibition, and combinations thereof.

In a specific embodiment, a method of detecting presence of influenza virus in a sample while minimizing false positives due to presence of one or more other pathogens in the sample is provided, the method comprising: (a) providing a sample suspected of comprising influenza virus; (b) contacting the sample with a substrate for indicating NA enzymatic activity; and (c) measuring NA enzymatic activity at a plurality of pH values ranging from about 4 to about 10, wherein: (i) significant NA enzymatic activity at a pH of about 4 indicates the presence of a pathogen other than influenza virus in the sample; (ii) significant NA enzymatic activity at a pH of about 7 coupled with significantly diminished NA enzymatic activity at a pH of about 9 indicates the presence of influenza virus in the sample; and (iii) substantially similar NA enzymatic activity at a pH of from about 6 to about 10 indicates the presence of a pathogen other than influenza virus in the sample.

In another embodiment, a method of detecting presence of influenza virus in a sample while minimizing false positives due to presence of one or more other pathogens in the sample is provided, the method comprising: (a) providing a sample suspected of comprising influenza virus; (b) contacting the sample with a substrate for indicating NA enzymatic activity; (c) measuring NA enzymatic activity in the presence and absence of an anti-NanA antibody that hinders enzymatic activity of NanA; and (d) comparing NA enzymatic activity in the presence and absence of the anti-NanA antibody, wherein: (i) substantially similar NA enzymatic activity in the presence and absence of the anti-NanA antibody indicates the presence of influenza virus in the sample; and (ii) significant NA enzymatic activity in the absence of the anti-NanA antibody coupled with significantly diminished NA enzymatic activity in the presence of the anti-NanA antibody indicates the presence of a pathogen other than influenza virus in the sample.

In another embodiment, a method of detecting presence of influenza virus in a sample while minimizing false positives due to presence of one or more other pathogens in the sample is provided, the method comprising: (a) providing a sample suspected of comprising influenza virus; (b) subjecting the sample to a size fractionation technique whereby pathogens substantially larger than influenza virus are removed from the sample; (c) contacting the sample with a substrate for indicating NA enzymatic activity; and (d) measuring NA enzymatic activity, wherein significant NA enzymatic activity indicates presence of influenza virus in the sample.

In another embodiment, a method of detecting presence of influenza virus in a sample while minimizing false positives due to presence of one or more other pathogens in the sample is provided, the method comprising: (a) providing a sample suspected of comprising influenza virus; (b) providing a solid support comprising an immobilized receptor that binds HA; (c) contacting the immobilized receptor with the sample, whereby influenza HA binds the immobilized receptor and forms a complex; (d) contacting the complex with a substrate for indicating NA enzymatic activity; and (e) measuring NA enzymatic activity, wherein significant NA enzymatic activity indicates the presence of influenza virus in the sample.

In another embodiment, a method of detecting presence of influenza virus in a sample while minimizing false positives due to presence of one or more other pathogens in the sample is provided, the method comprising: (a) providing a sample suspected of comprising influenza virus; (b) contacting the sample with a substrate for indicating NA enzymatic activity; and (c) measuring NA enzymatic activity in the presence and absence of a sulfonic acid-containing buffer, wherein: (i) substantially similar NA enzymatic activity in the presence and absence of the sulfonic acid-containing buffer indicates the presence of influenza virus in the sample; and (ii) significant NA enzymatic activity in the absence of the sulfonic acid-containing buffer coupled with significantly diminished NA enzymatic activity in the presence of the sulfonic acid-containing buffer indicates the presence of a pathogen other than influenza virus in the sample.

These and other objects, features, embodiments, and advantages will become apparent to those of ordinary skill in the art from a reading of the following detailed description and the appended claims.

DETAILED DESCRIPTION OF THE INVENTION

Figure 1:
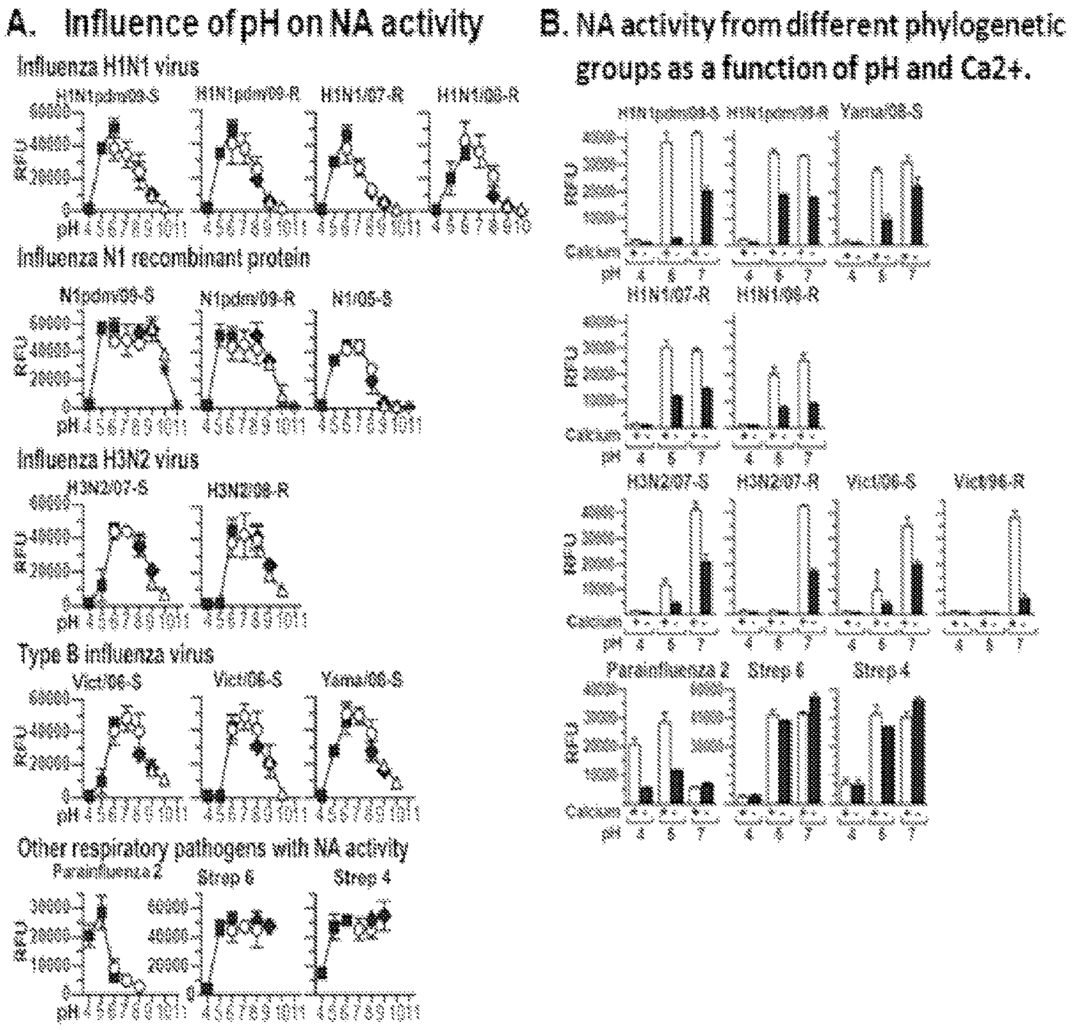
FIG. 1. NA enzymatic activity of different phylogenetic groups. (A) shows influence of pH in 0.1 mM $Ca^{2+}$; (B) shows NA enzymatic activity as a function of pH in the presence or absence of $Ca^{2+}$ by addition of 25 mM EDTA. Results are from at least 3 independent experiments. Error bars indicate standard deviation (SD).

The details of one or more embodiments of the presently-disclosed subject matter are set forth in this document. Modifications to embodiments described in this document, and other embodiments, will be evident to those of ordinary skill in the art after a study of the information provided herein.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, pH, size, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

For the purposes of describing and defining the present disclosure it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

The term "sample," as used herein, refers to a test sample or a biological sample, e.g., a clinical sample obtained from a patient. In certain embodiments, the sample is suspected of comprising influenza virus, another respiratory pathogen, or influenza virus and/or another respiratory pathogen. The skilled artisan will appreciate that a variety of biological samples are suitable for use in the presently-disclosed methods, including but not limited to saliva, nasal mucus, pharyngeal excretions, sputum, nasal and/or throat swabs, nasal and/or throat washes or aspirate, oral fluid, or lower respiratory tract specimen (bronchoalveolar lavage fluid, bronchial aspirates, bronchial washes, endotracheal aspirates or washes, tracheal aspirates, lung tissue), cell culture supernatant, cell culture extracts, adherent cells, suspension cells, tissue culture media, cloacal/fecal specimen, and the like.

The term "false positive," as used herein, refers to a test result that is erroneously classified in a positive category (as of diagnosis) because of imperfect testing methods or procedures. For example, in one embodiment, a false positive test result is a test results that erroneously reports the presence of influenza virus in a sample because of imperfect testing methods.

The methods presently disclosed permit the skilled artisan to measure NA enzymatic activity in a sample, under one or more differentiating conditions, in order to detect the presence of influenza virus for diagnostic purposes. The term "differentiating condition," as used herein, refers to a test variable that permits the skilled artisan to specifically detect influenza in a sample and/or distinguish influenza from other pathogens in a sample based on one or more distinguishing characteristics. In certain embodiments, the differentiating condition is selected from the group consisting of pH, binding to anti-NanA antibody, size exclusion, hemagglutinin (HA) binding, chemical inhibition, and combinations thereof.

The term "substrate for indicating NA enzymatic activity," as used herein, refers to a compound that is acted upon by the NA enzyme and elicits a measurable response. In certain embodiments, the substrate is selected from a colorimetric substrate, a fluorogenic substrate, and a luminescent substrate. In a specific embodiment, the substrate is 2'-(4-methylumbelliferyl)-a-D-N-acetylneuraminic acid (MUNANA).

The term "fluid based assay," as used herein, refers to assays performed in a liquid reaction environment. Exemplary fluid based assays include, for example, determining NA enzymatic activity in a test tube, microtiter plate well, or other vessel in which a fluid can be contained.

The term "chromatography based assay," as used herein, refers to assays performed by introducing liquid onto a solid support. Exemplary chromatography based assays include, for example, lateral or vertical flow diagnostic platforms such as single-channel or two-way lateral flow assays, or paper-based assays.

The term "neuraminidase inhibitor," as used herein, refers to a compound that inhibits the enzymatic activity of NA, and more specifically influenza NA. In certain embodiments, the neuraminidase inhibitor is selected from the group consisting of oseltamivir (Tamiflu®) and zanamivir (Relenza®).

In one embodiment, a method of detecting presence of influenza virus in a sample while minimizing false positives due to presence of one or more other pathogens in the sample is provided, the method comprising measuring the enzymatic activity of neuraminidase (NA) in the sample under one or more differentiating conditions selected from the group consisting of pH, binding to anti-NanA antibody, size exclusion, hemagglutinin (HA) binding, chemical inhibition, and combinations thereof.

NA enzymatic activity in any of the methods disclosed herein can be measured using a variety of techniques known to the skilled artisan. In one embodiment, NA enzymatic activity is measured by contacting the sample with a substrate for indicating NA enzymatic activity. The substrate is acted upon by NA in a manner that elicits a measurable or quantifiable response that correlates to NA enzymatic activity of the pathogen. A variety of pathogens express a protein having NA activity and elicit a response in the presence of a substrate for indicating NA enzymatic activity. For example, influenza, parainfluenza, and *S. pneumoniae* all express NA activities (in the case of *S. pneumoniae*, the NA enzyme is called NanA) which elicit a measurable response in the presence of a substrate for indicating NA enzymatic activity. However, NA enzymatic activity for these and other respiratory pathogens varies under the differentiating conditions described herein, permitting the skilled artisan to specifically detect influenza and direct patient care.

In one embodiment, the substrate is selected from the group consisting of a colorimetric substrate, a fluorogenic substrate, and a luminescent substrate. In the case of a colorimetric substrate, NA chemically alters the substrate and elicits a color response that is perceived by the skilled artisan and correlated to NA enzymatic activity. The color response can be observed by eye or interpreted using devices and/or software available for use with colorimetric substrates. In one embodiment, the difference or distance between two colors can be quantified and measured in terms of delta E, or change in sensation. Examples of suitable colorimetric substrates include, for example, 5-bromo-4-chloro-3-indolyl α-D-N-acetylneuraminic acid (X-NeuAc) and 2-O-(p-nitrophenyl)-α-D-N-acetylneuraminic acid (pNP-NeuAc).

In the case of a fluorogenic substrate, NA chemically alters the substrate and elicits a fluorescent response that is quantified by the skilled artisan and correlated to NA enzymatic activity. Any number of known fluorogenic substrates can be used in the disclosed methods. In a specific embodiment, the fluorogenic substrate is 2'-(4-methylumbelliferyl)-a-D-N-acetylneuraminic acid (MUNANA) and fluorescence is quantified at an excitation wavelength of 350 nm and an emission wavelength of 460 nm. The optimum pH for MUNANA is about pH 8-9, and thus in some embodiments test samples may be adjusted to pH 8-9 prior to reading fluorescence.

In the case of a luminescent substrate, NA chemically alters the substrate and elicits a luminescent response that is perceived and/or quantified by the skilled artisan and correlated to NA enzymatic activity. In one embodiment, the luminescent substrate is selected from the group consisting of 2-chloro-5-(4-methoxyspiro {1,2-dioxetane-3,2'-(5-chloro)tricyclo[3.3.1.1]decan}-4-yl-phenyl-5-acetamido-3,5-dideoxy-α-D-glycero-D-galacto-2-nonulopyranoside) onate (NA-Star, Applied Biosystems) and (sodium (3-chloro-5-(4-methoxyspiro {1,2-dioxetane-3,2'-(5-chloro) tricyclo[3.3.1.13,7]decan}-4-yl-phenyl 5-acetamido-3,5-dideoxy-α-D-glycero-D-galacto-2-nonulopyranoside) onate) (NA-XTD™, Applied Biosystems). Luminescence is quantified using a luminometer or other light-detecting device.

Measuring NA Enzymatic Activity Under Differentiating pH Conditions

Measuring NA enzymatic activity in a sample over a range of pH values provides a method of specifically detecting influenza virus and distinguishing influenza from other pathogens in a sample. When tested over a range of pH values, influenza NA enzymatic activity peaks at a pH of from about 6 to about 8, showing comparatively decreased NA enzymatic activity above about pH 8 and below about pH 6. For example, as shown in FIG. 1(A), it is noted that influenza NA enzymatic activity, as measured in RFU, resembles a bell curve that peaks from about pH 6 to about pH 8 and is comparatively diminished at pH values above about 8 and below about 6. More specifically, influenza NA enzymatic activity peaks at about pH 7 and is comparatively diminished at a pH of about 9. Conversely, parainfluenza NA activity peaks at about pH 4-5 and is comparatively diminished at pH values above about pH 5. *S. pneumoniae* NA activity peaks at about pH 5, but remains steady over a range of higher pH values, from about pH 5 to about pH 10.

Accordingly, a method of detecting presence of influenza virus in a sample while minimizing false positives due to presence of one or more other pathogens in the sample is provided, the method comprising: (a) providing a sample suspected of comprising influenza virus; (b) contacting the sample with a substrate for indicating NA enzymatic activity; and (c) measuring NA enzymatic activity at a plurality of pH values ranging from about 4 to about 10, wherein: (i) significant NA enzymatic activity at a pH of about 4 indicates the presence of a pathogen other than influenza virus in the sample; (ii) significant NA enzymatic activity at a pH of about 7 coupled with significantly diminished NA enzymatic activity at a pH of about 9 indicates the presence of influenza virus in the sample; and (iii) substantially similar NA enzymatic activity at a pH of from about 6 to about 10 indicates the presence of a pathogen other than influenza virus in the sample. In one embodiment, significant NA enzymatic activity at a pH of about 4 indicates the presence of parainfluenza virus in the sample. In another embodiment, substantially similar NA enzymatic activity at a pH of from about 6 to about 10 indicates the presence of *Streptococcus pneumoniae* in the sample.

The skilled artisan will appreciate that pH can be adjusted in the present methods using a variety of methods known in the art. For example, pH can be controlled through the use of the appropriate buffer solutions, the selection of which is within the purview of the skilled artisan. In certain embodiments, sodium acetate buffer is useful for measuring NA enzymatic activities at pH 4-6. Phosphate buffered saline (PBS) is useful for measuring NA enzymatic activities at pH 6-8. Tris(hydroxymethyl)aminomethane (Tris) is useful for measuring NA enzymatic activities pH 8-9. Other suitable buffers include, but are not limited to, succinate buffer, citrate buffer, acetate buffer, 4-(2-Hydroxyethyl)piperazine-1-ethanesulfonic acid (HEPES) buffer, 3-(N-morpholino) propanesulfonic acid hemisodium salt, 4-Morpholinepropanesulfonic acid (MOPS) buffer, and the like. All pH values are commonly adjusted using concentrated stocks of acid or base, such as NaOH and HCl. In another embodiment, measurement of NA enzymatic activity is carried out in the presence of calcium.

The presence or absence of calcium in the NA enzymatic activity assay is another factor useful in differentiating influenza virus from other potential pathogens. NA of influenza and parainfluenza has calcium binding sites, such that absence or removal of calcium from the reaction environment produces comparatively inhibited NA enzymatic activity. Conversely, *S. pneumoniae* NanA lacks calcium binding sites and is unaffected by the absence or removal of calcium from the reaction environment. Accordingly, provided herein is a method of detecting presence of influenza virus in a sample while minimizing false positives due to presence of one or more other pathogens in the sample, the method comprising: (a) providing a sample suspected of comprising influenza virus; (b) contacting the sample with a substrate for indicating NA enzymatic activity in the presence and absence of calcium; and (c) measuring NA enzymatic activity at a plurality of pH values ranging from about 4 to about 10, wherein: (i) significant NA enzymatic activity at a pH of about 4 in the presence of calcium coupled with significantly diminished NA enzymatic activity at a pH of about 4 in the absence of calcium indicates the presence of a pathogen other than influenza virus in the sample; (ii) significant NA enzymatic activity at a pH of about 7 in the presence of calcium coupled with significantly diminished NA enzymatic activity at a pH of about 7 in the absence of calcium indicates the presence of influenza virus in the sample; and (iii) substantially similar NA enzymatic activity in the presence and absence of calcium at a pH of from about 6 to about 10 indicates the presence of a pathogen other than influenza virus in the sample. In one embodiment, significant NA enzymatic activity at a pH of about 4 in the presence of calcium coupled with significantly diminished NA enzymatic activity at a pH of about 4 in the absence of calcium indicates the presence of parainfluenza virus in the sample. In another embodiment, substantially similar NA enzymatic activity in the presence and absence of calcium at a pH of from about 6 to about 10 indicates the presence of *S. pneumoniae* in the sample.

In one embodiment, the absence of calcium is achieved by the addition of a calcium chelator, such as ethylenediaminetetraacetic acid (EDTA) or ethylene glycol tetraacetic acid (EGTA), to the reaction matrix. It is appreciated that *S. pneumoniae* NanA enzymatic activity is substantially similar over a range of pH values of from about 6 to about 10, such that NA enzymatic activity in the presence and absence of calcium could be evaluated at any pH in that range (e.g., about 6, about 7, about 8, about 9, about 10, or any fractional pH within the range).

It is also appreciated that the methods disclosed herein are suitable for application to a variety of test platforms, including fluid based and chromatography based platforms.

Measuring NA Enzymatic Activity in the Presence and Absence of Anti-NanA Antibody Unlike NA of influenza, the bacterial NanA of *S. pneumoniae* does not undergo antigenic variation and is structurally divergent from NA. Thus, antibodies can be generated that bind to and hinder activity of NanA from all human *S. pneumoniae* isolates, without affecting the NA enzymatic activity of influenza. Such antibodies can be used in diagnostic platforms to increase the specificity for influenza. For example, antibodies to NanA can be used either to physically remove *S. pneumoniae* from the diagnostic specimen, or alternatively, neutralizing antibodies can be used to inhibit the enzymatic activity of NanA without affecting the NA activity of influenza. In certain embodiments, anti-NanA antibody sterically hinders NanA activity.

Accordingly, in one embodiment, a method of detecting presence of influenza virus in a sample while minimizing false positives due to presence of one or more other pathogens in the sample is provided, the method comprising: (a) providing a sample suspected of comprising influenza virus; (b) contacting the sample with a substrate for indicating NA enzymatic activity; (c) measuring NA enzymatic activity in the presence and absence of an anti-NanA antibody that hinders enzymatic activity of NanA; and (d) comparing NA enzymatic activity in the presence and absence of the anti-NanA antibody, wherein: (i) substantially similar NA enzymatic activity in the presence and absence of the anti-NanA antibody indicates the presence of influenza virus in the sample; and (ii) significant NA enzymatic activity in the absence of the anti-NanA antibody coupled with significantly diminished NA enzymatic activity in the presence of the anti-NanA antibody indicates the presence of a pathogen other than influenza virus in the sample. In this method, the anti-NanA antibody neutralizes at least a portion of any NanA present in the sample, while leaving influenza NA enzymatic activity unaffected, such that a relative decrease in observed NA enzymatic activity in the presence of the anti-NanA antibody indicates presence of *S. pneumoniae* in the sample. Thus, in a more specific embodiment, significant NA enzymatic activity in the absence of the anti-NanA antibody coupled with significantly diminished NA enzymatic activity in the presence of the anti-NanA antibody indicates the presence of *S. pneumoniae* in the sample.

The skilled artisan will appreciate that pH adjustment may be desired in order to facilitate an accurate measurement of NA enzymatic activity for different pathogens. For example, in order to distinguish between influenza and parainfluenza, the reaction pH may be optimized for influenza (i.e., pH of from about 6 to about 8, or more specifically about pH 7) in order to minimize false positives from parainfluenza virus. The optimized pH for influenza will also capture results for *S. pneumoniae*, which can then be excluded through application of other differentiating conditions disclosed herein.

It is also appreciated that the methods disclosed herein are suitable for application to a variety of test platforms, including fluid based and chromatography based platforms.

Suitable anti-NanA antibodies will hinder the enzymatic activity of NanA and thus effectively neutralize at least a portion of NanA present in a sample. Generation of antibodies is well within the purview of the skilled artisan and can be accomplished through a variety of methods known in the art. Either polyclonal or monoclonal antibodies are suitable for use in the disclosed methods. In a specific embodiment, polyclonal antibodies are raised by inoculating an animal such as a rabbit, mouse, or goat with purified NanA protein. Polyclonal antibodies are then purified from animal sera. In a specific embodiment, an animal is inoculated with purified NanA protein. In a very specific embodiment, the purified NanA protein comprises SEQ ID NO: 4 or a fragment thereof. Alternatively, monoclonal antibodies are generated via hybridoma cell production, purification, and/or cloning. Recombinant monoclonal antibodies are also suitable for use and can be engineered using known cloning techniques. Methods of generating polyclonal and monoclonal antibodies are well known in the art. See, for example, Andrew J. T. George, et al., *Diagnostic and Therapeutic Antibodies* (1st ed. 2010). The skilled artisan will be able to generate and select an anti-NanA antibody that binds to NanA and hinders NanA activity. In one embodiment, the anti-NanA antibody binds to NanA protein comprising SEQ ID NO: 4 or a fragment thereof.

Measuring NA Enzymatic Activity Under Differentiating Size Exclusion Conditions The NanA activity of *S. pneumoniae* remains associated with the intact bacteria. The influenza virus particle is 0.080-0.120 micrometers in diameter. In contrast, individual *S. pneumoniae* cells are ten times larger, typically 0.8 to 1.25 micrometers in diameter. Size fractionation techniques are thus useful in separating larger pathogens from the relatively smaller influenza virus, in order to specifically detect influenza virus in a sample.

Accordingly, a method of detecting presence of influenza virus in a sample while minimizing false positives due to presence of one or more other pathogens in the sample is provided, the method comprising: (a) providing a sample suspected of comprising influenza virus; (b) subjecting the sample to a size fractionation technique whereby pathogens substantially larger than influenza virus are removed from the sample; (c) contacting the sample with a substrate for indicating NA enzymatic activity; and (d) measuring NA enzymatic activity, wherein significant NA enzymatic activity indicates presence of influenza virus in the sample.

The skilled artisan will appreciate that pH adjustment may be desired in order to facilitate an accurate measurement of NA enzymatic activity for different pathogens. For example, in order to distinguish between influenza and parainfluenza, the reaction pH may be optimized for influenza (i.e., pH of from about 6 to about 8, or more specifically about pH 7) in order to minimize false positives from parainfluenza virus. The optimized pH for influenza will also capture results for *S. pneumoniae*, which can then be excluded through application of other differentiating conditions disclosed herein. A variety of size fractionation techniques are suitable for use in the instantly disclosed methods. In one embodiment, samples are filtered through membranes having a pore size that permits removal of pathogens substantially larger than influenza virus from the sample, while permitting influenza virus to pass through the filter pores. In a specific embodiment, a suitable filter has a pore size of from about 0.2 microns to about 0.8 microns. Other suitable size fractionation techniques, including centrifugation, chromatography, and the like, are known in the art, the selection of which is within the purview of the skilled artisan.

Measuring NA Enzymatic Activity in the Presence of a Receptor that Binds HA

Figure 5:
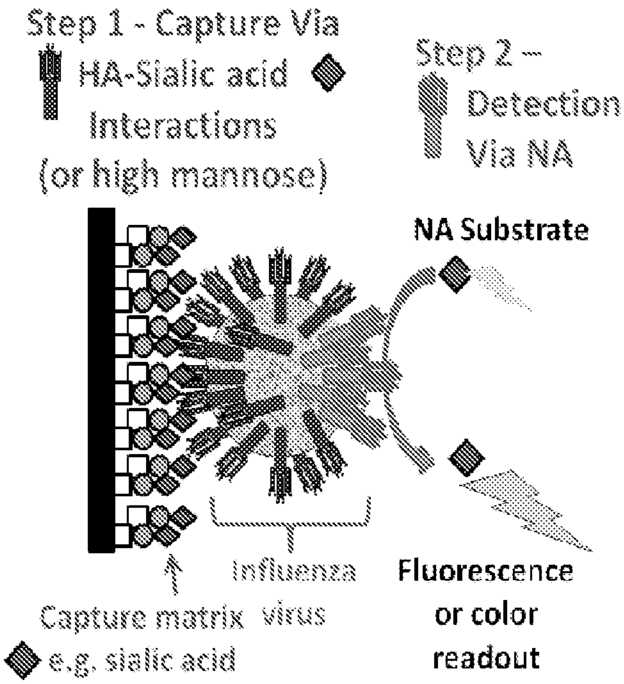
FIG. 5. Influenza diagnosis via innate viral properties. In step 1, virus is captured via hemagglutinin (HA)-sialic acid interactions or NA, HA high-mannose interactions. In step two, bound virus is contacted with a detecting substrate and NA enzymatic activity is measured.

As illustrated in FIG. 5, influenza virus capture via the influenza sialic acid binding protein HA can be employed to remove NA enzymatic activity not due to influenza from clinical samples. Other pathogens, such as *S. pneumoniae*, do not possess sialic acid binding activity.

Accordingly, a method of detecting presence of influenza virus in a sample while minimizing false positives due to presence of one or more other pathogens in the sample is provided, the method comprising: (a) providing a sample suspected of comprising influenza virus; (b) providing a solid support comprising an immobilized receptor that binds HA; (c) contacting the immobilized receptor with the sample, whereby influenza HA binds the immobilized receptor and forms a complex; (d) contacting the complex with a substrate for indicating NA enzymatic activity; and (e) measuring NA enzymatic activity, wherein significant NA enzymatic activity indicates the presence of influenza virus in the sample.

In a further embodiment, a washing step is carried out after contacting the immobilized receptor with the sample, such that un-bound pathogens are washed from the solid support prior to reading the NA enzymatic activity.

The skilled artisan will appreciate that pH adjustment may be desired in order to facilitate an accurate measurement of NA enzymatic activity for different pathogens. For example, in order to distinguish between influenza and parainfluenza, the reaction pH may be optimized for influenza (i.e., pH of from about 6 to about 8, or more specifically about pH 7) in order to minimize false positives from parainfluenza virus. The optimized pH for influenza will also capture results for *S. pneumoniae*, which can then be excluded through application of other differentiating conditions disclosed herein.

A variety of solid supports are suitable for use in immobilizing receptors that bind HA. For example, microtiter plates or chromatography paper are suitable for use in the present methods. Receptors that bind HA are immobilized on the appropriate solid support using a variety of methods, such as hydrophilic interactions, hydrophobic interactions, protein-protein interactions, amine-binding, and the like.

Various receptors that bind HA are known in the art and may be used in conjunction with the present methods. Suitable receptors include, but are not limited to, sialylated protein receptors such as fetuin and asialofetuin; mannose binding receptors such as dendritic cell-specific intercellular adhesion molecule grabbing non-integrin (DC-SIGN), DC-SIGN receptor (DC-SIGNR), mouse DC SIGN (mDC-SIGN), macrophage-mannose receptor (MMR), and mannose-binding lectin (MBL); and other binding proteins, such as epidermal growth factor receptor (EGFR) and galectin.

It is also appreciated that the methods disclosed herein are suitable for application to a variety of test platforms, including fluid based and chromatography based platforms

Measuring NA Enzymatic Activity in the Presence of Chemical Inhibitors

Sulfonic acid-containing buffers inhibit the neuraminidase activity of *S. pneumoniae*, while the NA activity of influenza is relatively resistant to such sulfonic acid. Measuring NA enzymatic activity in the presence and absence of chemical inhibitors comprising sulfonic acid, cyclohexyl rings, morpholinyl rings, or derivatives thereof provides another method of detecting influenza and differentiating influenza from other pathogens in a sample, including *S. pneumoniae*.

Accordingly, a method of detecting presence of influenza virus in a sample while minimizing false positives due to presence of one or more other pathogens in the sample is provided, the method comprising: (a) providing a sample suspected of comprising influenza virus; (b) contacting the sample with a substrate for indicating NA enzymatic activity; and (c) measuring NA enzymatic activity in the presence and absence of a sulfonic acid-containing buffer, wherein: (i) substantially similar NA enzymatic activity in the presence and absence of the sulfonic acid-containing buffer indicates the presence of influenza virus in the sample; and (ii) significant NA enzymatic activity in the absence of the sulfonic acid-containing buffer coupled with significantly diminished NA enzymatic activity in the presence of the sulfonic acid-containing buffer indicates the presence of a pathogen other than influenza virus in the sample. In a specific embodiment, significant NA enzymatic activity in the absence of the sulfonic acid-containing buffer coupled with significantly diminished NA enzymatic activity in the presence of the sulfonic acid-containing buffer indicates the presence of *S. pneumoniae* in the sample.

The skilled artisan will appreciate that pH adjustment may be desired in order to facilitate an accurate measurement of NA enzymatic activity for different pathogens. For example, in order to distinguish between influenza and parainfluenza, the reaction pH may be optimized for influenza (i.e., pH of from about 6 to about 8, or more specifically about pH 7) in order to minimize false positives from parainfluenza virus. The optimized pH for influenza will also capture results for *S. pneumoniae*, which can then be excluded through application of other differentiating conditions disclosed herein.

Various sulfonic acid-containing buffers are suitable for use in the present methods, including, but not limited to, N-cyclohexyl-2-aminoethanesulfonic acid (CHES) and N-cyclohexyl-3-aminopropanesulfonic acid (CAPS), N-cyclohexyl-2-hydroxyl-3-aminopropanesulfonic acid (CAPSO), 4-[cyclohexylamino]-1-butansulphonic acid (CABS), 3-(N-morpholino) propanesulfonic acid, 4-morpholinepropane sulfonic acid (MOPS), 3-morpholino-2-hydroxypropanesulfonic acid sodium salt, and 3-(N-morpholinyl)-2-hydroxypropanesulfonic acid (MOPSO), and combinations thereof. In a specific embodiment, the sulfonic acid-containing buffer is CHES or CAPS.

It is also appreciated that the methods disclosed herein are suitable for application to a variety of test platforms, including fluid based and chromatography based platforms

Determining Susceptibility to NA Inhibitors

Determining susceptibility of pathogens to NA inhibitors such as oseltamivir and zanamivir is also useful in distinguishing influenza from other pathogens in a sample and directing patient care. Recent strains of influenza have demonstrated resistance to oseltamivir and/or zanamivir, and pathogens such as *S. pneumoniae* are uniformly resistant to oseltamivir and zanamivir. Identifying isolates susceptible to treatment by NA inhibitors will direct effective patient care and avoid increasing prevalence of viral resistant strains in the population due to over-prescribing NA inhibitors.

Accordingly, any of the presently disclosed methods may further comprise: measuring NA enzymatic activity in the presence and absence of a neuraminidase (NA) inhibitor; and comparing NA enzymatic activity in the presence and absence of the NA inhibitor, wherein: (i) substantially similar NA enzymatic activity in the presence and absence of the NA inhibitor indicates the presence of a pathogen in the sample that is not susceptible to therapeutic treatment with the NA inhibitor; and (ii) significant NA enzymatic activity in the absence of the NA inhibitor coupled with significantly diminished NA enzymatic activity in the presence of the NA inhibitor indicates the presence of a pathogen in the sample that is susceptible to therapeutic treatment with the NA inhibitor.

Any NA inhibitor known or later developed is suitable for use in the methods described herein. In a specific embodiment, the NA inhibitor is selected from the group consisting of oseltamivir (Tamiflu®) and zanamivir (Relenza®). Other suitable NA inhibitors include peramivir, R-125489, and other NA inhibitors currently in development.

The skilled artisan is able to use the information pertaining to susceptibility of the clinical isolate to NA inhibitors in order to direct patient care, i.e., prescribe treatment with a suitable NA inhibitor if the patient's sample tests positive for influenza susceptible to NA inhibitor treatment.

Combining Differentiating Conditions

It is important to note that any of the preceding methods of specifically detecting influenza virus using differentiating conditions can be employed alone or in combination with one or more of the other methods disclosed herein. Combination assays include, but are not limited to, an assay that combines pH differentiation and size exclusion, or an assay that combines pH differentiation and anti-NanA antibody neutralization and/or chemical inhibition, and the like. Any number of the disclosed differentiating conditions can be combined to develop a highly specific method of detecting and distinguishing influenza viruses from other pathogens in a sample.

EXAMPLES

The following examples are given by way of illustration and are in no way intended to limit the scope of the present invention.

Example 1

Differentiation of Influenza, Parainfluenza, and *S. pneumoniae* Based on Measurement of NA Enzymatic Activity Under Differentiating Conditions of pH, Calcium, and Susceptibility to NA Inhibitors Viral and bacterial strains assessed in this study are characterized in Table 1, below.

TABLE 1

Characteristics of viral and bacterial strains

| Virus strain | Ct[a] | NA act. RFU[b] | HA Titer | FFU per mL[c] | % of max NA act. + EDTA (pH)[d] | Osel $IC_{50}$ (nM) | Zan $IC_{50}$ (nM) |
|---|---|---|---|---|---|---|---|
| H1N1 strains | | | | | | | |
| A/California/07/09 (H1N1pdm/09-S) | 23 | 6600 | 320 | $7 \times 10^8$ | 44% (pH 6-7) | 0.9 | 1.3 |

TABLE 1-continued

Characteristics of viral and bacterial strains

| Virus strain | Ct[a] | NA act. RFU[b] | HA Titer | FFU per mL[c] | % of max NA act. + EDTA (pH)[d] | Osel $IC_{50}$ (nM) | Zan $IC_{50}$ (nM) |
|---|---|---|---|---|---|---|---|
| A/North Carolina/39/09 (H1N1pdm/09-R) | 25 | 5300 | 80 | $5 \times 10^6$ | 63% (pH 6-7) | 125 | 1.2 |
| A/Brisbane/59/07-Like (H1N1/07-R) | 25 | 5000 | 160 | $3 \times 10^7$ | 54% (pH 6) | 2220 | 3.3 |
| A/Florida/21/08 (H1N1/08-R) | 25 | 4700 | 320 | $2 \times 10^6$ | 36% (pH 6) | 1729 | 2.2 |
| Recombinant N1 protein (purified recombinant protein expressed in human cells, obtained from Sino Biological Inc. http://www.sinobiological.com/) | | | | | | | |
| A/California/04/09 (N1pdm/09-S) | n/a | 16000 | n/a[1] | n/a | 94% (pH 6-8) | 62 | 25 |
| A/California/04/09 (N1pdm/09-R) | n/a | 13000 | n/a | n/a | 94% (pH 6-8) | 758 | 3.7 |
| A/Anhui/01/05 (N1/05-S) | n/a | 12900 | n/a | n/a | 43% (pH 6-7) | 13 | 5.6 |
| H3N2 strains | | | | | | | |
| A/Brisbane/10/07-Like (H3N2/07-S) | 23 | 6700 | 40 | $3 \times 10^6$ | 50% (pH 7) | 0.6 | 1.6 |
| A/Texas/12/07 (H3N2/07-R) | 25 | 6800 | 160 | $4 \times 10^6$ | 61% (pH 7) | 15 | 2.6 |
| Type B strains | | | | | | | |
| B/Brisbane/60/08 (Vict/06-S) | 28 | 5800 | 320 | $5 \times 10^7$ | 92% (pH 7) | 13 | 4.1 |
| B/Memphis/20/96 (Vict/96-R) | 25 | 5900 | 320 | $9 \times 10^3$ | 25% (pH 7) | 104 | 6.3 |
| B/Florida/04/06 (Yama/08-S) | 27 | 5000 | 320 | $9 \times 10^5$ | 88% (pH 7) | 19 | 4.5 |
| Parainfluenza virus Type 2 | n/a | 4800 | ND | ND | 27% (pH 5) | ND | ND |
| *S. pneumoniae* | | | | | | | |
| ATCC 6305 (Strep 6) | n/a | 5000 | n/a | n/a | 112% (pH 7) | ND | ND |
| ATCC 49619 (Strep 4) | n/a | 5000 | n/a | n/a | 108% (pH 7) | ND | ND |

[a]Rounded threshold cycle (Ct) values determined by RT-PCR in viral samples at 1 to 1000 dilution.
[b]Rounded average of RFU/h/μL in NA assay in PBS, pH 7 for all influenza and *S. pneumoniae* strains, and sodium acetate buffer, pH 5 for Parainfluenza type 2.
[c]Fluorescent Focus units were determined using the fluorescent focus-forming assay
[d]% of maximal NA activity obtained in presence of 25 mM EDTA.
Osel: Oseltamivir,
Zan: Zanamivir,
ND: Not determined,
n/a, not applicable.

In order to assess the effects of pH on viral strains, viruses were diluted 50-fold (2 μL samples diluted to final volume of 100 μL) in each of five buffers, each containing 10 μM MUNANA, 20 mM NaCl, and 0.1 mM calcium. MUNANA, NaCl, and $CaCl_2$ stock solutions were prepared to a final concentration of 10 mM, 5 M, and 1 M, respectively and diluted to final concentration. Sodium acetate buffer was used for studies at pH 4, 5, and 6. Phosphate buffered saline (PBS) was used for studies at pH 6, 7, and 8. Tris(hydroxymethyl)aminomethane (Tris) buffer was used for studies at pH 8 and 9. N-cyclohexyl-2-aminomethanesulfonic acid (CHES) buffer (50 mM) was used for studies at pH 9 and 10. 3-(cyclohexylamino)-1-propanesulfonic acid (CAPS) buffer (50 mM) was used for studies at pH 10 and 11. All pH values were adjusted using concentrated stocks of NaOH and HCl.

*S. pneumoniae* was grown overnight on blood agar and colonies were suspended to an optical density (OD) of 1 at 600 nm in water. 50-fold dilutions (2 μl of viral samples diluted into a final volume of 100 μl) were made in each of the reaction buffers. All reactions were incubated at 37° C. for 3 h. The pH optimum for detecting fluorescence was determined to be pH 8-9 and all samples were adjusted to pH 8 using 1 M Tris buffer before fluorescence was determined. NA activity was examined using the fluorescent substrate, MUNANA (Sigma-Aldrich, Inc., USA). Fluorescent-methylumbelliferone was measured with FLX-800 fluorimeter (BioTek, USA) using excitation and emission wavelengths of 350 and 460 nm, respectively. Relative fluorescent units (RFU) were used to quantify NA enzymatic activity. Results are shown in FIG. 1(A).

In the presence of 0.1 mM calcium, influenza strains displayed significant NA enzymatic activity between pH 6 and 7. In contrast, the NA enzymatic activity of parainfluenza type 2 is optimal at pH 5, with less than 25% maximal activity at pH 7. Intact *S. pneumoniae* NA displayed a broad pH optimum spectrum of 6-9. It is noted that broad tolerance to pH range is not seen with purified NanA protein, and hence would not have been predicted from published studies. While not desiring to be bound by theory, it is believed that the observed tolerance is attributed to the ability of live bacteria to buffer their environment. It is also noted that the pH activity profiles of purified recombinant NA were different from the pH profiles of the same NA protein when present on intact virus. Again, while not desiring to be bound by theory, it is believed that the difference is attributed to the failure of recombinant NA to form NA tetramers displayed on the viral particle. Results of FIG. 1(A) suggest unique pH activity profiles for intact, viable pathogens which were not predicted from published studies using purified protein.

In studies examining calcium dependence, influenza viruses were diluted 50-fold (2 μl viral samples were diluted to a final volume of 100 μl) and parainfluenza viruses were diluted 20-fold (5 μl viral samples were diluted to a final volume of 100 μl) in 4-(2-hydroxyethyl)-1-piperazineethanesulfonic acid (HEPES) buffer (50 mM HEPES, 200 mM NaCl; pH 7 for influenza virus and pH 6 for parainfluenza virus) containing 10 μM MUNANA, with different concentrations of $CaCl_2$. 0 mM of $CaCl_2$ was designated when 25 mM ethylenediaminetetraacetic acid (EDTA) was added. RFUs were used to quantify NA enzymatic activity and percentages to NA enzymatic activity were calculated, defining 100% as the largest value in each data set. NA enzymatic activity was examined in the absence of calcium at pH 4, 5, and 7. Results are shown in FIG. 1(B).

Results indicate the activity of *S. pneumoniae* NanA, which does lacks a calcium binding site, was not affected by the absence of calcium in the reaction matrix. The NA enzymatic activity of influenza and parainfluenza strains was inhibited by the removal of calcium. See FIG. 1(B).

Figure 2:
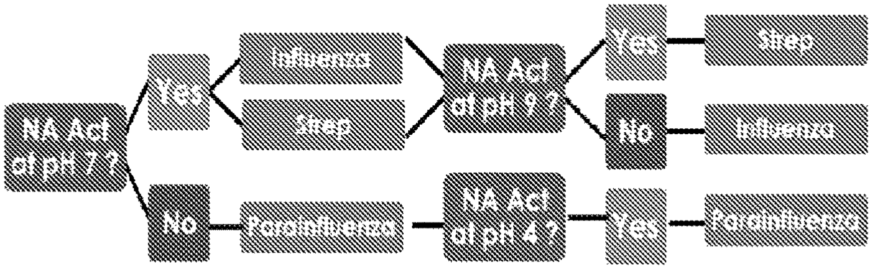
FIG. 2. Flow chart for distinguishing NA enzymatic activity of influenza from other pathogens, under differentiating pH conditions.

FIG. 2 summarizes how different enzymatic signatures of NA activity can be used to differentiate influenza from other respiratory pathogens.

Example 2

Figure 10:
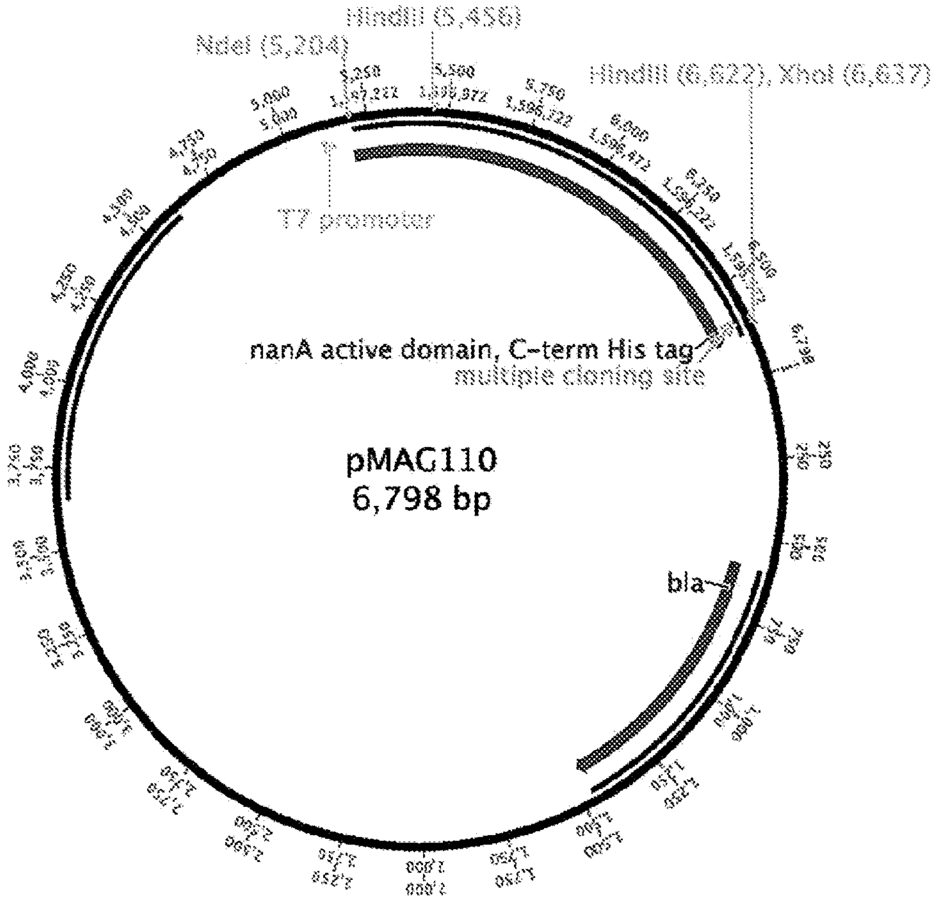
FIG. 10. Restriction map of pMAG110, including 1.4 kb NanA insert.

NA Enzymatic Activity of Influenza and *S. pneumoniae* in the Presence and Absence of Anti-NanA Antibody The enzymatic domain of NanA was expressed as a His-tagged protein and used to produce polyclonal rabbit antiserum for NanA. The C-terminal domain of *S. pneumoniae* NanA (AE005672) was expressed with a hexahistidine tag for purposes of purification and antibody production. The template source was genomic DNA from *S. pneumoniae* strain TIGR4 (ATCC BAA-334). The vector was pET-22b (+). The NanA catalytic domain, PDB 2YA4 (NanA residues 307-777) was amplified using the following PCR primers: NanA_F2 (with 5'NdeI site) 5'-CATATGGCTTTAACAGAGAAAACG-3' (SEQ ID NO: 1) and NanA_R2 (with 3' HindIII site, stop codon removed to clone into pET-22b(+) with C-terminal hexahistidine tag) 5'-AAGCTTATTTTTGCTCAAAAATTCCC-3' (SEQ ID NO: 2). The PCR amplification product was run on a 0.8% agarose gel and a 1.4 kb band was excised, purified, and sequenced to verify correct NanA sequence. NanA sequence (SEQ ID NO: 3) was cloned into pET-22b(+) using standard procedures to create pMAG110, pET-22b(+) vector with a 1.4 kb NanA insert when digested with NdeI and XhoI. A restriction map of pMAG110 is shown in FIG. 10.

A 50 μl-aliquot of Rosetta™(DE3)pLysS competent cells was thawed and 1 μl of pMAG110 plasmid containing the catalytic region of NanA was added for transformation. Transformants were selected on Luria broth-agar with 50 μg/ml of carbenicillin. 100 ml of L-broth containing 50 μg/ml of carbenicillin and 34 μg/ml of chloramphenicol was inoculated and incubated overnight at 37° C. The next day 25 ml of the overnight culture was used to inoculate 1 L of LB-broth containing 50 μg/ml of carbenicillin and 34 μg/ml of chloramphenicol and incubated at 37° C. When the $OD_{600}$ reached 1, NanA production was induced with 1 mM IPTG and 2% ethanol, followed by shaking incubation for 16 h at 20° C. Cells were centrifuged at 6400 g for 15 minutes. The pellet was suspended in PBS buffer containing 20 mM imidazole and cells were broken by repeated freeze-thaw cycles and finally sonicated for 15 minutes. Cell debris was removed by centrifugation at 15000 g for 40 minutes and supernatant was filter-sterilized with 0.45 μM filters. NanA crude extract was dialyzed in PBS buffer with 20 mM imidazole.

NanA was isolated from the crude extract using HisTrap™ HP columns. Dialyzed sample was allowed to pass through the column, followed by four washes with 5-column volumes of four different buffers of PBS (pH 7.4 with 20 mM, 100 mM, 200 mM, and 500 mM imidazole, respectively). Fractions of 5 ml were collected and then analyzed by SDS-PAGE and Western blot. Fractions containing NanA were pooled together and concentrated using Amicon Ultra-15 centrifugal filter with a cutoff of 50 kDa. Ion exchange purification was performed using Q-sepharose (GE Healthcare) packed into a gravity flow column of 10 ml. The NanA sample was dialyzed in 50 mM TRIS pH 8 with 50 mM NaCl overnight. The dialyzed sample was allowed to pass through the Q-sepharose column. The column was washed four times with 10-column volume four different buffers of 50 mM TRIS pH 8 with 50 mM, 100 mM, 500 mM, and 1 M NaCl, respectively. Fractions of 5 ml were collected and then analyzed by SDS-PAGE and Western blot. Fractions containing NanA were pooled together and concentrated using Amicon Ultra-15 centrifugal filter with a cut off of 50 kDa. Purified NanA protein (SEQ ID NO: 4) was used to produce polyclonal sera in rabbits.

Antibody Mediated Inhibition of NanA

Figure 3:
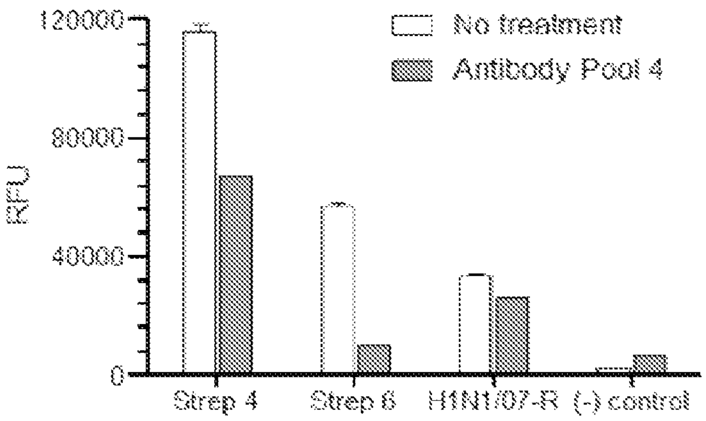
FIG. 3. (A) depicts NA enzymatic activity of influenza and *S. pneumoniae* based in the presence and absence of anti-NanA antibody. Results show anti-NanA antibody inhibits NA enzymatic activity of *S. pneumoniae*, but not influenza virus; (B) depicts inhibition of NA enzymatic activity of *S. pneumoniae* in the presence of increasing concentrations of polyclonal antibody (0-500 μg). A no protein control (0) or purified of recombinant NanA (5-20 μgimp from *S. pneumoniae* was immobilized to microtiter plates. Results show about 50% inhibition at high antibody concentrations.
Figure 3:
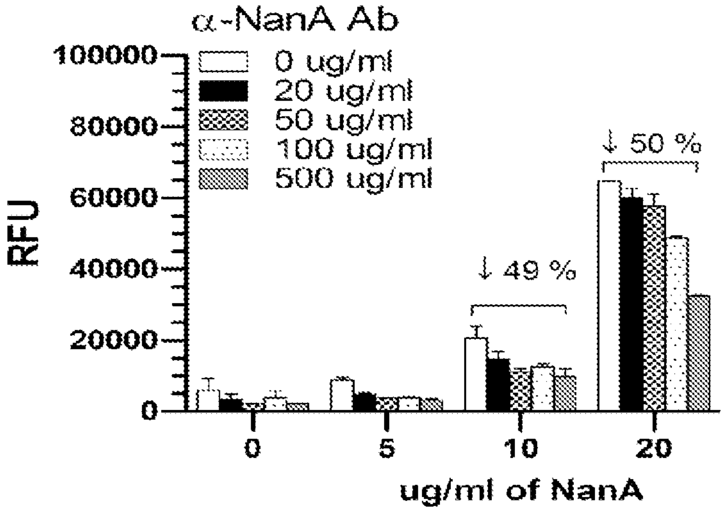

NA activity of influenza and *S. pneumoniae* were measured in PBS reaction buffer pH 6.5 containing 0.1 mM calcium and >1 mg/ml concentration of purified anti-NanA antibody. *S. pneumoniae* was grown in a blood agar plate and 1 colony from the overnight culture of *S. pneumoniae* was suspended into 1 ml of in water. Each *S. pneumoniae* suspension was further diluted 50-fold in reaction buffer in each well. Influenza viruses were diluted 50-fold in reaction buffer (2 μl of viral samples were diluted to a final volume of 100 μl). Both *S. pneumoniae* and influenza were incubated for 15 min with anti-NanA antibody in the reaction buffer. After incubation, 10 μl of 100 nM of MUNANA substrate was added to a final concentration 10 nM and fluorescence was read after 90 min. Results are shown in FIG. 3(A). Results show that anti-NanA antibody causes significant inhibition of NanA, with minimal effect on the NA activity of influenza A.

Next, different concentrations (5, 10, and 20 μg/ml) of recombinant NanA were immobilized on hydrophilic microtiter plates (Microfluor® 2, Thermo Scientific, USA) using 100 mM bicarbonate/carbonate buffer at pH 9 overnight at 4° C. After coating, all plates were washed with cold PBS and blocked with 2% BSA in PBS for 1 hour at room temperature. After blocking, plates were washed and incubated with different concentrations of anti-NanA antibody diluted in PBS buffer pH 6.5 with 0.1 mM calcium and incubated for 30 min. After incubation, 10 μl of 100 nM of MUNANA substrate was added to a final concentration 10 nM and fluorescence was read after 90 min. Results are shown in FIG. 3(B). Results indicated that increasing amounts of antibody correlates to increasing inhibition of NanA activity, with about 50% inhibition at the highest dose of antibody, 500 μg/ml.

In summary, these studies demonstrate that neutralizing antibodies to the *S. pneumoniae* NanA protein can be generated and used to specifically inhibit the bacterial NanA enzyme, while influenza NA enzyme remains substantially active.

Example 3

Differentiating Influenza from Other Pathogens by Size Exclusion 50-fold dilutions of influenza virus were prepared by mixing 80 μl of each viral stock into 4 ml distilled water. *S. pneumoniae* was grown overnight on blood agar and four colonies were suspended into 4 ml water. Half of the sample was filtered using cellulose acetate filters with different pore sizes (0.8, 0.45, and 0.22 μm). NA activity of both filtered and non-filtered dilutions was measured in PBS reaction buffer pH 6.5 containing 0.1 mM calcium and 10 nM MUNANA. 90 μl of viral dilutions were incubated with 10 μl of 10×PBS reaction buffer. For *S. pneumoniae,* 2 μl of the dilution were incubated in 100 μl reaction buffer. All reactions were incubated at room temperature and fluorescence was determined after 90 minutes.

Figure 4:
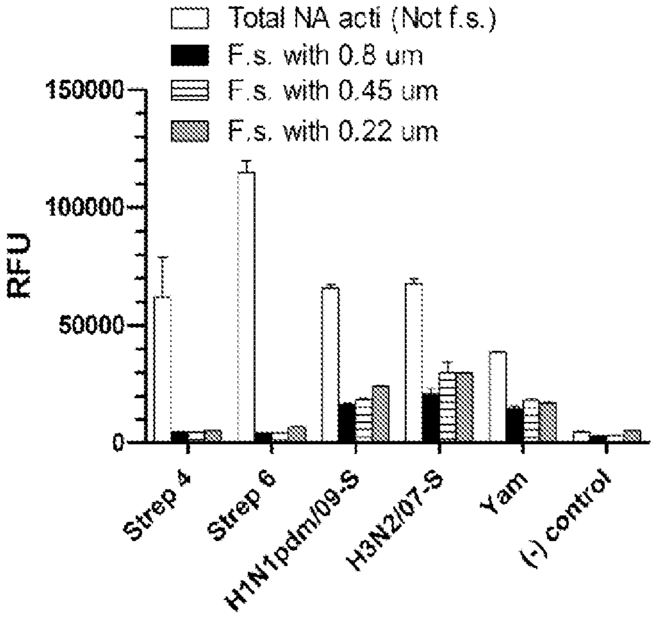
FIG. 4. NA enzymatic activity after filtering suspensions containing *S. pneumoniae* or influenza virus through membranes of various pore sizes (0.8 μm, 0.45 μm, 0.22 μm) is depicted. Results indicated a loss of *S. pneumoniae* NanA enzymatic activity post-filtration, and a partial reduction of influenza NA enzymatic activity post-filtration.

As shown in FIG. 4, all of the NanA activity of *S. pneumoniae* was lost when the bacteria were filtered through 0.8, 0.45 or 0.22 micron filters. In contrast, much of the NA activity was retained preparations of influenza A (H1N1, H3N2) or influenza B (Yam, Yamagata) were filtered. Results indicate filtering, or other suitable size fractionation techniques, are suitable for use in differentiating influenza virus NA activity from bacterial NA activity.

Example 4

Differentiation of Pathogens Via Hemagglutinin (HA) Binding to Ligands

Biotinylated synthetic glycans and biotinylated fetuin were dissolved in phosphate buffered saline pH 7 and immobilized on streptavidin coated plates (SigmaScreen™, Sigma-Aldrich, USA) overnight at 4° C. Host recombinant proteins at 2.5 μg/ml were immobilized overnight at 4° C. on hydrophilic microtiter plates (Microfluor® 2, Thermo Scientific, USA) using 100 mM bicarbonate/carbonate buffer at pH 9. After coating, all plates were washed with cold PBS and blocked with 2% BSA in PBS for 1 hour at 4° C. After blocking, plates were washed and incubated with 1/30 dilutions of virus for 1 hour. Virus binding was evaluated at 4° C. where the viral neuraminidase is not active to avoid the need to add NA inhibitors. The plates were washed with cold PBS to remove unbound virus and virus binding was determined by measuring NA activity at 37° C. NA activity reaction buffer consisted of PBS at pH 6.5 containing 0.1 mM $CaCl_2$ and 10 μM MUNANA (Sigma-Aldrich, Inc., USA). Reactions were incubated for 3 hours at 37° C. Samples were adjusted to pH 9.5 using 0.7 M N-cyclohexyl-2-aminoethanesulfonic acid (CHES) buffer. Fluorescence of the released 4-methylumbelliferone was measured with a FLX-800 fluorimeter (BioTek, USA) using excitation and emission wavelengths of 350 and 460 nm, respectively. Fetuin and MBL were used to determine the limit of detection of the capturing assay, using dilutions of virus: 1/30, 1/50, 1/90, 1/150 1/270, and 1/450.

Figure 6:
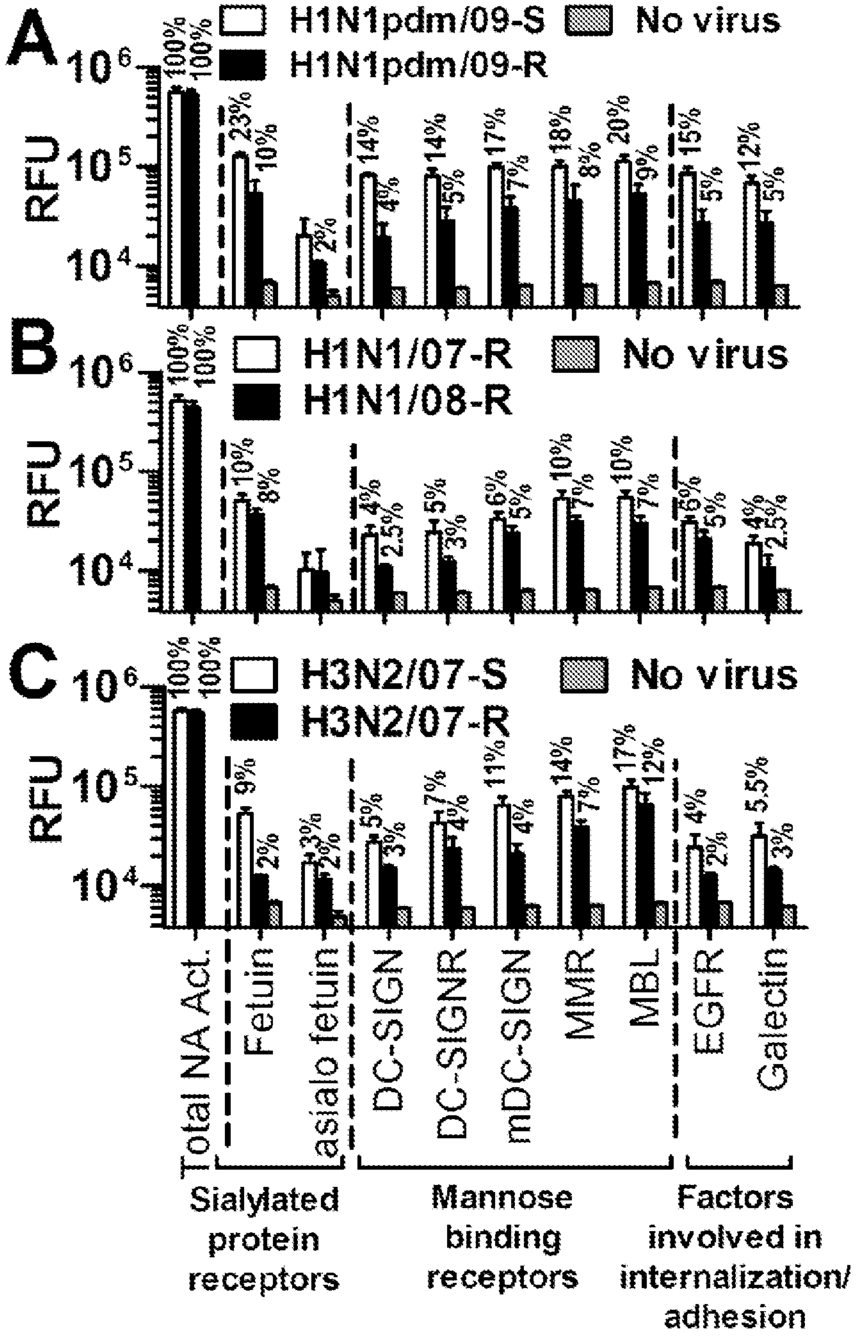
FIG. 6. Capture of influenza virus by receptor mimics and recombinant host proteins. Protein immobilized on microtiter plates was used to capture influenza virus and bound virus was detected by measuring NA enzymatic activity. (A) 2009 pandemic influenza; (B) influenza H1N1 (from 2007 and 2008); (C) influenza H3N2. At least 3 independent repeats, error bar indicate SD. Percentage is indicated for values significantly greater than negative control at P≤0.02.

Capture of influenza was assessed using synthetic glycans (e.g. NeuAcα2-3Gal or NeuAcα2-6Gal) and host proteins, including fetuin, immobilized on microtiter plates by a modified ELISA, where bound virus was detected using the fluorogenic NA substrate. Fetuin is a highly sialylated protein isolated from bovine serum. Up to 9% total weight of fetuin can be attributed to NeuAc, displaying a multi-antennary N-linked glycosylation pattern with terminal NeuAcα2-3Gal or NeuAcα2-6Gal. Tested ligands included fetuin, asialofetuin, DC-SIGN, DC-SIGNR, mDC-SIGN, MMR, MBL, EGFR, and galectin. Results are shown in FIG. 6. Tested viruses included H1N1pdm/09-S, H1N1pdm/09-R (FIG. 6(A)), H1N1/07-R, H1N1/08-R (FIG. 6(B)), and H3N2/07-S, H3N2/07-R (FIG. 6(C).

Since the relative fluorescent unit (RFU) values spanned in a wide range, a logarithmic scale was used in the y-axis to display very low values, and percent (%) capture is indicated for values which were significantly greater than the no virus control. Sialic acid is the most important determinant for receptor recognition, and viruses bound fetuin better than asialofetuin (fetuin with the sialic acid moieties removed). One exception is the H3N2/07-R strain which showed little capture by either molecule (see FIG. 6(C)), which is consistent with other published reports for viruses from this period.

Proteins which bind to high mannose glycosylation included DC-SIGN, DC-SIGNR, mDC-SIGN, MMR, and MBL. MBL and MMR, which strongly bind to terminal mannose residues, were able to capture more virus than DC-SIGN analogs. MBL receptor was the best capturing factor among all mannose binding receptors (FIG. 6). EGFR (reported to be involved in viral internalization) and galectin (reported to block viral adhesion to host cells), are considered protein factors that play a role in the interaction between influenza and host cells. EGFR and galectin were the least effective for viral capture.

Figure 7:
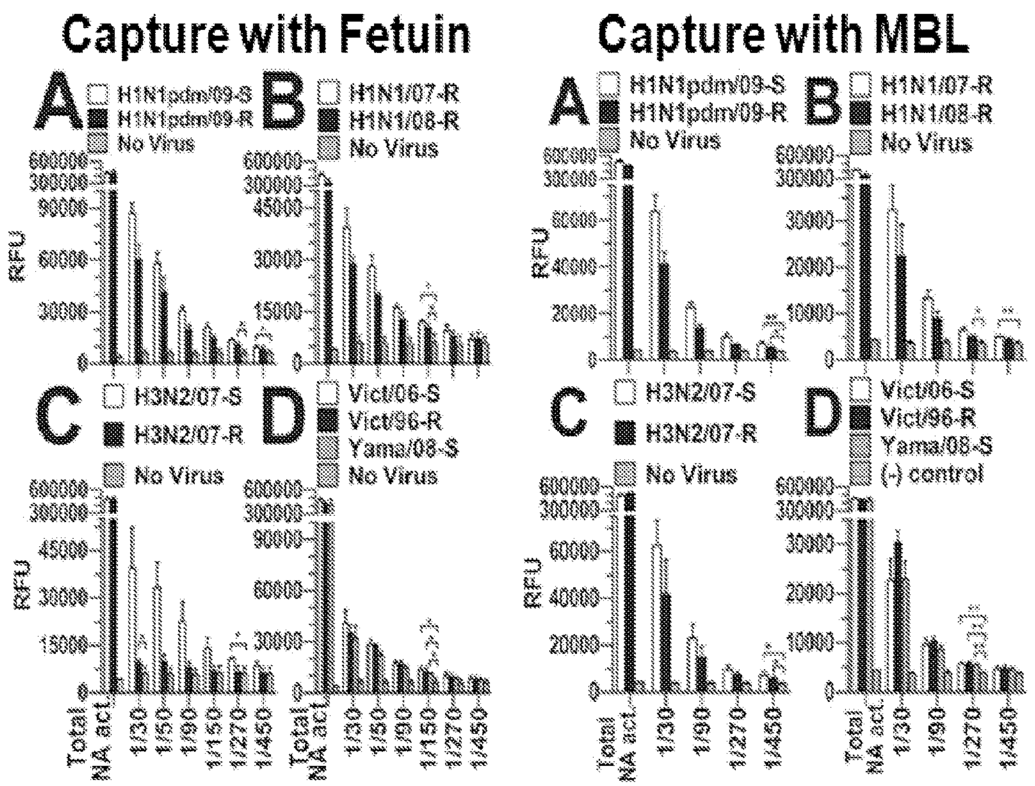
FIG. 7. Limit of detection of fetuin and MBL as capturing agents for influenza virus. Influenza strains were paired by similarities in different panels and capture was assessed by detecting NA enzymatic activity. (A) Pandemic influenza H1N1pdm/09 strains; (B) Influenza H1N1 (2007/2008); (C) Influenza H3N2 strains; (D) Influenza type B. Total NA act. represents NA enzymatic activity of virus at 1/30 dilution. Results are from at least 3 independent experiments. Error bars indicate SD. Statistical differences were calculated by the two-tailed Student's t-test using GraphPad Prism™ 5. The maximum dilution of virus giving statistical significant difference from negative control is indicated with * for a P≤0.02 and ** for a P≤0.008.

Virus dilution studies were performed to determine the limit of detection using the two best capturing factors, fetuin and MBL (FIG. 7). Fetuin captured virus at 150-450 fold dilutions, while MBL captured virus at 270-450 fold dilutions. These values are only slightly less than the 500-fold dilution which is the limit of detection for NA enzymatic activity without viral capture (data not shown). Most significant is the ability of MBL to detect H3N2/07-R down to 450-fold dilution, compared to a 30-fold dilution limit using fetuin.

Example 5

NA Enzymatic Activity in the Presence of Sulfonic Acid-Containing Buffers

Figure 11:
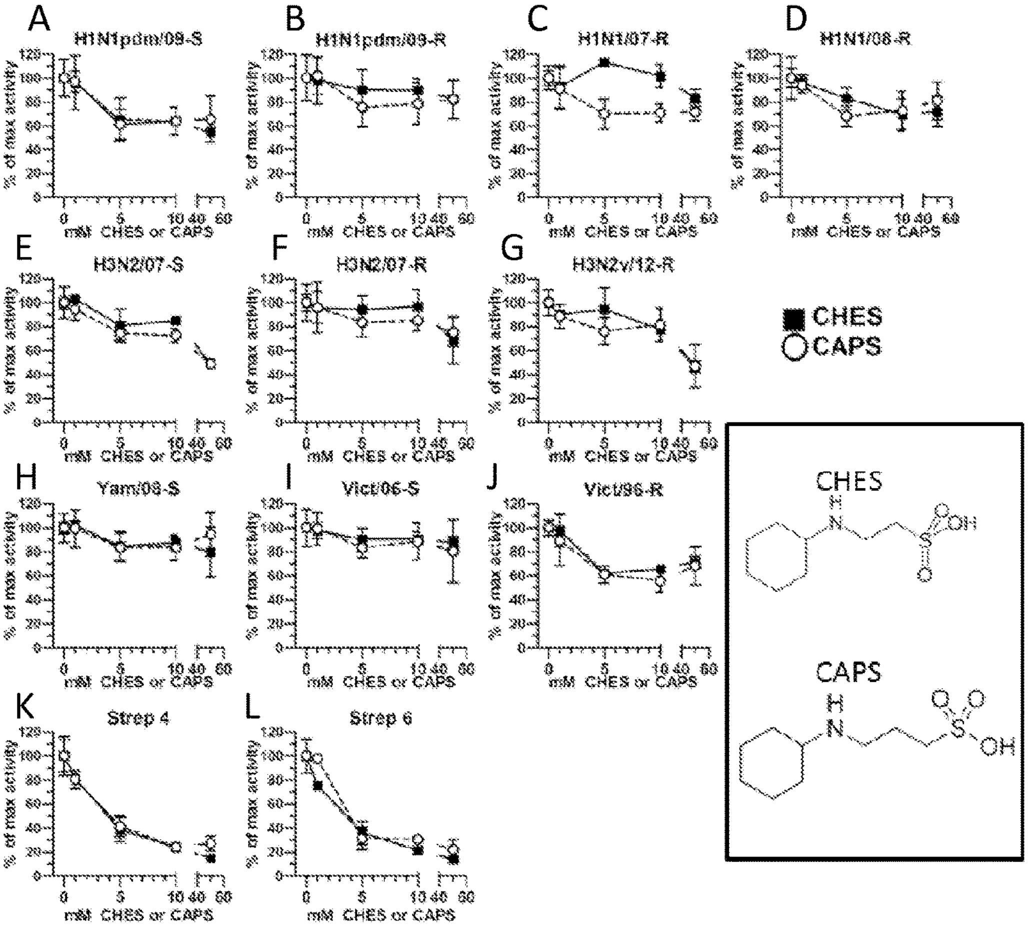
FIG. 11. Inhibition of pathogens by CHES (■) and CAPS (○). (A) H1N1pdm/09-S; (B) H1N1pdm/09-R; (C) H1N1/07-R; (D) H1N1/08-R; (E) H3N2/07-S; (F) H3N2/07-R; (G) H3N2v/12-R; (H) Yam/08-S; (I) Vict/06-S; (J) Vict/96-R; (K) Strep 4; and (L) Strep 6.

NA enzymatic activity of a variety of pathogens was measured in PBS pH 7 containing different concentrations of CHES and CAPS buffers. NA enzymatic activity was examined using the fluorescent substrate MUNANA. Influenza viruses were diluted 50-fold (2 μl of viral samples were diluted to a final volume of 100 μl). *S. pneumoniae* was grown overnight on blood agar and colonies were suspended to an optical density (OD) of 1 at 600 nm in water. 50-fold dilutions (2 μl of viral samples diluted into a final volume of 100 μl) were made in each of the reaction buffers. All reactions were incubated at room temperature for 90 minutes. RFUs were used to quantify NA activity and percentages to NA activity were calculated, defining 100% as the largest value in each data set. Results are shown in FIG. 11.

Results indicate that NA enzymatic activity of influenza is substantially resistant to 10 mM CHES, while the NanA activity of *S. pneumoniae* is severely reduced by 10 mM CHES. Results show that NanA can be distinguished from the NA of influenza by its susceptibility to CHES and CAPS inhibition.

Example 6

Comparison of NA Enzymatic Activity Assay Vs. Commercial Rapid Diagnostic Tests

Virus was suspended in nasal mucus from a healthy human donor, and NA detection using the fluorogenic substrate MUNANA was compared with three commercially available rapid diagnostic tests (Directigen™ (BD); Tru-Flu® (Meridian Bioscience, Inc.); and BinaxNOW® (Alere™).

Figure 8:
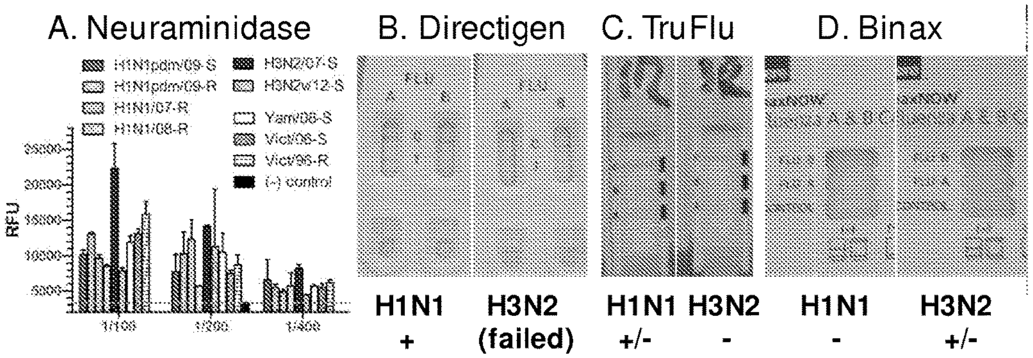
FIG. 8. Sensitivity of viral detection in 50% nasal mucus. (A) NA enzymatic activity of a panel of viruses at 1/200 dilution in 50% nasal mucus. (B)-(D) Detection of H1N1pdm/09-R and H3N2/07-R diluted 1/200 in 50% nasal mucus. (B) Directigen™ test kit; (C) TruFlu® test kit; (D) BinaxNOW® test kit.

For the commercially available rapid diagnostic influenza tests, 200-fold dilutions of influenza virus were prepared in normal human mucus diluted to 50% in 2×PBS reaction buffer (1×=PBS pH 6.5 with 0.1 mM calcium and 10 nM MUNANA). Commercial rapid tests were preformed according to manufacturers' instructions. For the NA enzymatic activity assay, different dilutions (1/100, 1/200 and 1/400) of influenza virus were prepared in 50% mucus 50% 2× reaction buffer as described above. NA enzymatic activity was measured at room temperature and fluorescence was determined after 90 minutes (negative control=NA enzymatic activity of normal mucus alone). Results are shown in FIG. 8.

In the NA enzymatic assay, all nine tested viruses displayed significantly more activity than the negative control. (FIG. 8(A)). In the commercial tests, controls are indicated by "C" or "control." Test results are labeled "T." "A" or "Flu A" indicates influenza A and "B" or "Flu B" indicates influenza B. The Directigen™ Flu A test for H3N2 failed to work, as evidenced by the lack of a result line in the control well (FIG. 8(B), second test). The controls of the other tests functioned properly. However, each of the commercially available tests failed to detect one of the viruses when suspended in 50% nasal mucus.

Results indicate that the NA enzymatic assay detects virus in human nasal mucus and meets or exceeds results from commercially available tests. Further, the NA enzymatic assay is insensitive to antigenic variation and is thus able to detect newly emerging viruses.

Example 7

Microfluidic Paper-Based Analytical Device for Detecting Presence of Influenza and Assessing Susceptibility to NA Inhibitor An assay capable of detecting the presence of influenza by monitoring neuraminidase activity and assessing viral susceptibility to the neuraminidase inhibitor, oseltamivir (Tamiflu®), was developed, using a wax-printed Microfluidic Paper-Based Analytical Device (μPAD). The device is fabricated using a Xerox® wax-based printer which prints the template directly onto Whatman #1 filter paper. The printed paper is transferred onto a hot plate which melts the wax pattern through the entire cross-section of the paper, creating hydrophilic (non-printed) and hydrophobic (wax-printed) areas for fluid control. Initial experiments used a 96-well format. The physical layout matches size and spacing of wells in a conventional 96-well microplate. While a conventional microplate normally requires over 604 of fluid per well, as little as 3 μL can fill the test area of the μPAD. Results are shown in FIG. 9.

The μPAD was validated using human seasonal influenza viruses known to have various susceptibility patterns to Tamiflu® (FIG. 9(A)). NA activity was detected using 5-Bromo-4-chloro-3-indolyl α-D-N-acetylneuraminic (X-NeuAc), which is enzymatically converted by NA from a colorless compound to an insoluble, intensely blue compound. The buffer/substrate solution was added to the device, followed by the addition of virus. 13 μL per test area was used (10 μL of buffer/substrate and 3 μL of virus solution). The device was incubated at room temperature with humidity and image analysis was performed. As seen in previous experiments, using the μPAD, influenza strains show optimal neuraminidase activity at about pH 7 in the presence of 0.1 mM $Ca^{2+}$ (pH 7+), but reduced neuraminidase activity at pH 4 and pH 9 (data not shown), demonstrating that the unique enzymatic signature of each NA type can be used to differentiate between different strains.

Figure 9:
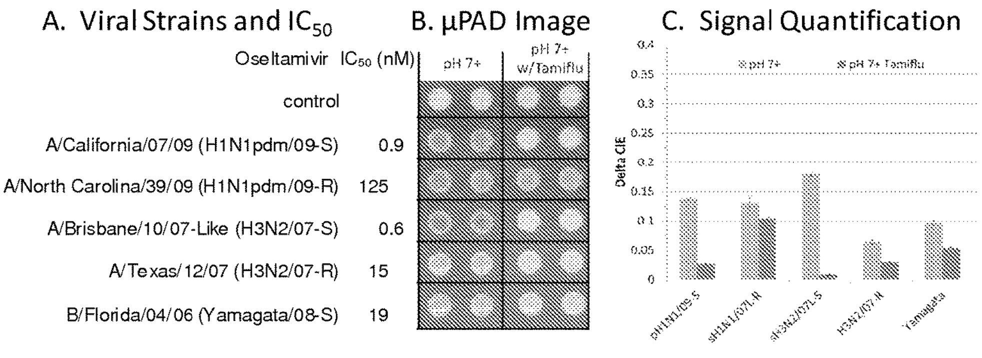
FIG. 9. NA activity assay for various influenza strains using a wax-printed, microfluidic paper-based analytical device (μPAD). (A) Viral strains and $IC_{50}$; (B) μPAD image at two buffer conditions (pH 7 and pH 7+ with Tamiflu® (350 nM oseltamivir carboxylate); (C) Comparison graph of the delta CIE color change (compared to negative control) from the digital image of (B).

To assess detection and susceptibility to Tamiflu®, duplicate wells were incubated with virus at pH 7 with or without 350 nM of the activated form of Tamiflu®, oseltamivir carboxylate (FIG. 9). Intense blue signal was seen for all of the virus-containing wells (FIG. 9(B), pH 7+), but not in the control wells lacking virus. In addition, reduced signal was observed in the wells supplemented with the active form of Tamiflu®, oseltamivir carboxylate (FIG. 9(B), pH 7+w/ Tamiflu®). The changes in signal intensity were validated by the quantification studies (FIG. 9(C)). An inverse correlation between the half maximal inhibitory concentration ($IC_{50}$) values determined in previous studies (FIG. 9(A)) and inhibition of signal was observed.

The μPAD test shows great promise as a simple, robust, inexpensive point-of-care device to detect the presence of influenza and predict susceptibility to neuraminidase-based antiviral drugs.

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

What is claimed is:

1. A method of diagnosing and treating influenza in a human patient, the method comprising:

(a) providing a biological sample obtained from the patient, wherein the sample is suspected of comprising influenza virus;

(b) subjecting the sample to size fractionation whereby pathogens larger than influenza virus are removed from the sample;

(c) contacting the sample with a substrate for indicating NA enzymatic activity, wherein said contacting is carried out under reaction conditions of from about pH 6 to about pH 8;

(d) measuring NA enzymatic activity in the sample, wherein detection of NA enzymatic activity indicates presence of influenza virus in the sample;

(e) diagnosing the patient with influenza when the presence of influenza virus in the sample is indicated; and (f) administering an antiviral drug selected from the group consisting of oseltamivir, zanamivir, peramivir, and R-125489 to the diagnosed patient.

2. The method of claim 1, wherein size fractionation comprises filtering with a filter having a pore size of from about 0.2 microns to about 0.8 microns.

3. The method of claim 1, wherein the substrate for indicating NA enzymatic activity is selected from the group consisting of a colorimetric substrate, a fluorogenic substrate, and a luminescent substrate.

4. The method of claim 3, wherein the substrate is 2'-(4-methylumbelliferyl)-a-D-N-acetylneuraminic acid (MUNANA) and measuring NA enzymatic activity comprises comparing relative fluorescent units (RFU).

* * * * *